United States Patent
Kost et al.

(10) Patent No.: US 10,350,235 B2
(45) Date of Patent: Jul. 16, 2019

(54) CATIONIC POLYSACCHARIDES FOR DELIVERY OF PHOSPHOINOSITIDES TO CELLS FOR THERAPEUTIC PURPOSE

(71) Applicant: Joseph Kost, Omer (IL)

(72) Inventors: Joseph Kost, Omer (IL); Riki Goldbart, Lehavim (IL); Tamar Traitel, Beer Sheva (IL); Nitzan Marelly, Rosh Ha-Ayin (IL); Assaf Rudich, Metar (IL); Etili Hollander, Caesarea (IL)

(73) Assignee: Joseph Kost, Omer (IL)

( * ) Notice: Subject to any disclaimer, the term of this patent is extended or adjusted under 35 U.S.C. 154(b) by 16 days.

(21) Appl. No.: 15/241,293

(22) Filed: Aug. 19, 2016

(65) Prior Publication Data
US 2017/0049900 A1 Feb. 23, 2017

Related U.S. Application Data

(60) Provisional application No. 62/206,921, filed on Aug. 19, 2015.

(51) Int. Cl.
*A61K 31/718* (2006.01)
*A61K 47/61* (2017.01)

(52) U.S. Cl.
CPC ............ *A61K 31/718* (2013.01); *A61K 47/61* (2017.08)

(58) Field of Classification Search
None
See application file for complete search history.

(56) References Cited

U.S. PATENT DOCUMENTS

| 4,031,307 A | 6/1977 | DeMartino et al. |
| 2015/0366979 A1* | 12/2015 | Kost ............. C12N 15/113 514/44 A |

FOREIGN PATENT DOCUMENTS

WO 200018949 A2 4/2000

OTHER PUBLICATIONS

Kale, S. D., Gu, B., Capelluto, D. G., Dou, D., Feldman, E., Rumore, A., . . . & Lawrence, C. B. (2010). External lipid PI3P mediates entry of eukaryotic pathogen effectors into plant and animal host cells. Cell, 142(2), 284-295. (Year: 2010).*
Nitzan Marelly et al; "Development of modified starch based complexes for PI3P delivery in order to overcome insulin resistance", The 9th Biennial meeting of the Israeli Chapter of the Controlled Release Society (ICRS)—Sep. 9-11, 2014—p. 48 in poster book + poster + presentation.
O. Felt et al; "Delivery of Antibiotics to the Eye Using a Positively Charged Polysaccharide as Vehicle" AAPS PharmSci 3(4) article 34. (2001).
Fischer et al; "A novel non-viral vector for DNA delivery based on low molecular weight, branched polyethylenimine: effect of molecular weight on transfection efficiency and cytotoxicity" Pharmaceutical research vol. 16. No. 8 pp. 1273-1279. (1999).
W.T. Godbey et al; "Poly(ethylenimine)-mediated gene delivery a!ects endothelial cell function and viability" Biomaterials 22 pp. 471-480. (2001).
Nitzan Marelly et al; "Overcoming Hepatic Insulin Resistance Using Modified Starch for ExogenousPI3P Delivery" Feb. 26, 2015 (jubilee convention of the Israeli Institute for chemical engineers (IICHE)) poster.
Nitzan Marelly et al; "Development and characterization of targeted delivery system based on PI3P and modified starch to overcome insulin resistance", workshop at the Weizmann Inst., Jul. 5-7, 2015.
Nitzan Marelly et al; "Up-Regulating Autophagy in Attempt to Overcome Insulin Resistance Using Quaternized Starch as PI3P Carrier", abstract sent, meeting Jul. 26-29, 2015 CRS, abstract available Jun. 26, 2015.
Sieradzki R et al; "Development and characterization of quaternized starch as a carrier for gene therapy applications" 2008, PhD thesis.
Ilana Kachko et al; "Polymeric Carrier-Mediated Intracellular Delivery of Phosphatidylinositol Trisphosphate to Overcome Insulin Resistance" AIChE100 Annual Meeting. Nov. 16-21, 2008, Philadelphia, PA.
Gordon A. Morris et al; "Polysaccharide drug delivery systems based on pectin and chitosan" Biotechnology and Genetic Engineering Reviews—vol. 27, pp. 257-284. (2010).
Paillard et al., Positively-charged, porous, polysaccharide nanoparticles loaded with anionic molecules behave as 'stealth' cationic nanocarriers, Pharm. Res. 27(1):pp. 126-133. (2010).
Shoichiro Ozaki et al: "Intracellular delivery of phosphoinositides and inositol phosphates using polyamine carriers" PNAS vol. 97 No. 21 pp. 11286-11291. (2000).
Dove et al., (1997) Osmotic stress activates phosphatidylinositol-3,5-bisphosphate synthesis. Nature 390(6656): 187-192.
Geresh et al., (2000) Chemical modifications of biopolymers: quaternization of the extracellular polysaccharide of the red microalga *Porphyridium* sp.. Carbohydrate Polymers 43(1): 75-80.
Ishiki et al., (2005) Insulin regulates the membrane arrival, fusion, and C-terminal unmasking of glucose transporter-4 via distinct phosphoinositides. J Biol Chem 280(31): 28792-28802.
Jia et al., (2001) Synthesis and antibacterial activities of quaternary ammonium salt of chitosan. Carbohydrate Research 333(1): 1-6.
Jiang et al., (1998) Membrane-permeant esters of phosphatidylinositol 3,4,5-trisphosphate. J Biol Chem 273(18): 11017-11024.
Li et al., (2004) Effect of molecular weight and degree of substitution of quaternary chitosan on its adsorption and flocculation properties for potential retention-aids in alkaline papermaking. Colloids and Surfaces A: Physicochemical and Engineering Aspects 242(1-3): 1-8.

(Continued)

*Primary Examiner* — Shaojia A Jiang
*Assistant Examiner* — Dale R Miller
(74) *Attorney, Agent, or Firm* — Vorys, Sater, Seymour and Pease

(57) ABSTRACT

The present invention provides a complex comprising at least one phosphoinositide and at least one positively charged modified polysaccharide, pharmaceutical compositions comprising the complex, methods for treatment of a disease, disorder or condition associated with impaired phosphoinositide-mediated signaling comprising administering the complex to an subject in need, and methods for (Continued)

delivery of a phosphoinositide into cells, comprising contacting the cells with the complex of the invention.

**9 Claims, 9 Drawing Sheets
(2 of 9 Drawing Sheet(s) Filed in Color)**

(56) References Cited

OTHER PUBLICATIONS

Patel et al., (2003) Intracellular segregation of phosphatidylinositol-3,4,5-trisphosphate by insulin-dependent actin remodeling in L6 skeletal muscle cells. Mol Cell Biol 23(13): 4611-4626.
Payrastre et al., (2001) Phosphoinositides: key players in cell signalling, in time and space. Cell Signal 13(6): 377-387.
Strawbridge et al., (2005) Phosphatidylinositol 4,5-bisphosphate reverses endothelin-1-induced insulin resistance via an actin-dependent mechanism. Diabetes 54(6): 1698-1705.
Sweeney et al., (2004) Intracellular delivery of phosphatidylinositol (3,4,5)-trisphosphate causes incorporation of glucose transporter 4 into the plasma membrane of muscle and fat cells without increasing glucose uptake. J Biol Chem 279(31): 32233-32242.
Vicinanza et al., (2015) PI(5)P regulates autophagosome biogenesis. Mol Cell 57(2): 219-234.
Yamashita et al., (2007) Functions of PI4P and sterol glucoside are necessary for the synthesis of a nascent membrane structure during pexophagy. Autophagy 3(1): 35-37.
Yu et al., (2007) Preparation and characterization of a quaternary ammonium derivative of konjac glucomannan. Carbohydrate Polymers 69(1): 29-40.
Yudovin-Farber et al., (2005) Quaternary ammonium polysaccharides for gene delivery. Bioconjugate Chem 16: 1196-1203.

* cited by examiner

Fig. 3A
Fig. 3B
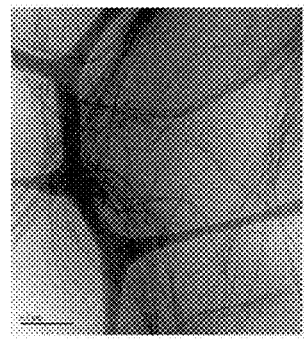
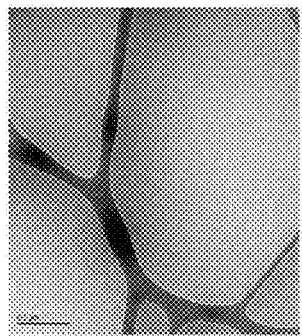
Fig. 3C
Fig. 3D
Fig. 3E
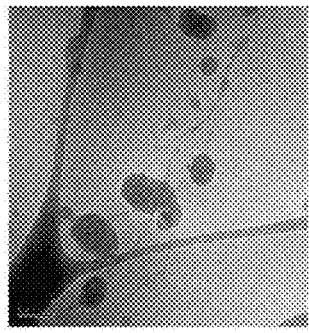
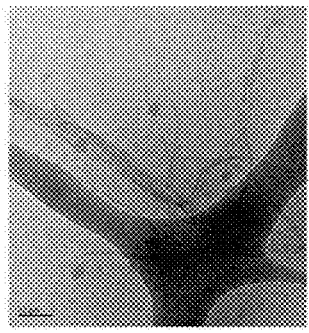
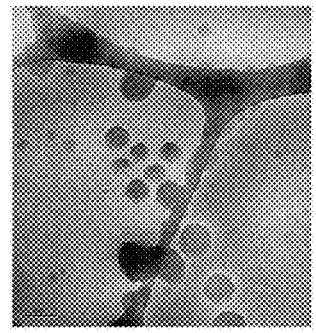

Fig. 6A
Fig. 6B
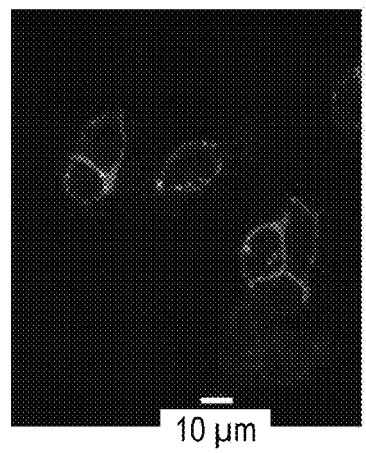
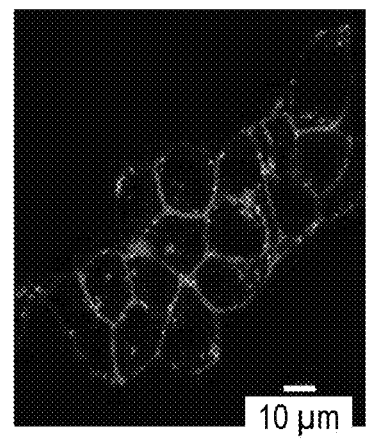
Fig. 6C
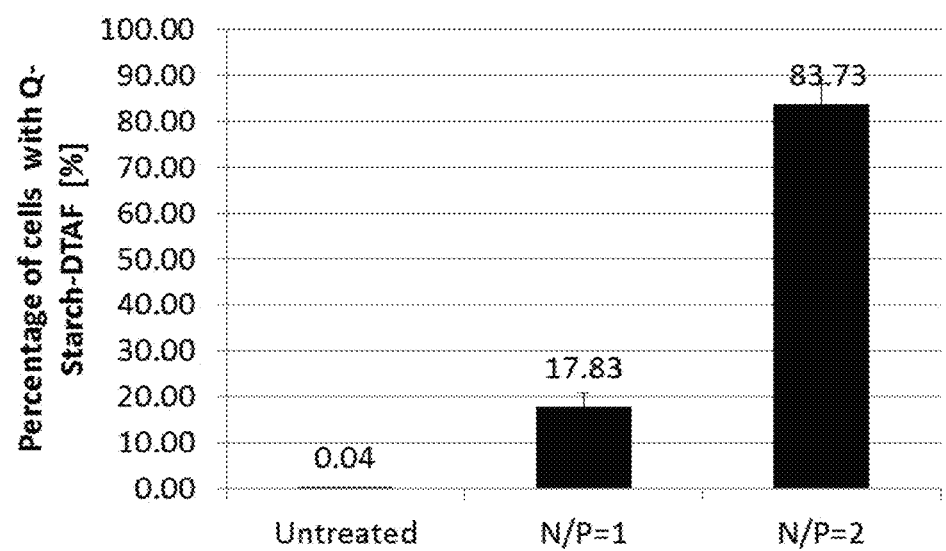

CATIONIC POLYSACCHARIDES FOR DELIVERY OF PHOSPHOINOSITIDES TO CELLS FOR THERAPEUTIC PURPOSE

CROSS REFERENCE TO RELATED APPLICATIONS

This application claims the benefit of U.S. Provisional Application Ser. No. 62/206,921 filed Aug. 19, 2015, the disclosure of which is expressly incorporated herein by reference.

FIELD OF THE INVENTION

The present invention relates to the use of modified positively charged polysaccharides for the delivery of phosphoinositides to mammalian cells and the treatment of diseases, disorders or conditions associated with impaired phosphoinositide-mediated signaling.

BACKGROUND OF THE INVENTION

Phosphoinositides (PIPs) are a group of inter-convertible lipid messengers harboring single, double or triple phosphoryl moieties on positions 3, 4 and/or 5 of their inositol ring. Although they account for a minor fraction of total cellular lipids, PIPs appear to be major second messengers in signaling networks by tyrosine kinase receptors of hormones and growth factors, by several G-coupled receptors, as well as by environmental cellular stresses. Bursts of increase in PI-3,4,5-$P_3$ ($PIP_3$), largely produced by 3' phosphorylation of PI-4,5-$P_2$ (phosphatidylinositol 4,5-bisphosphate) in a process catalyzed by phosphatidylinositol 3-kinase (PI 3-kinase), is a major signaling step mediating cellular functions as diverse as metabolism, cellular motility, gene regulation and cell survival (anti-apoptosis).

One example for PIPs involvement in mediating cellular function is its role in diabetes. Diabetes type II is characterized by insulin resistance which is a state of impaired metabolic response to insulin. Current pharmacological therapeutics is mostly based on activation or inhibition of enzymes or receptors, a strategy somewhat limited when the disease process involves impaired insulin signaling capacity. Phosphatidylinsoitol-3,4,5-trisphosphate ($PIP_3$), production induced by insulin, has now been shown to constitute a major lipid messenger in insulin-mediated metabolic actions in muscle and fat. Intracellular delivery of $PIP_3$ into cells would therefore be ideal for bypassing the signaling defect.

Altered skin wound healing is a common cause of morbidity and mortality among diabetic patients, caused in response to a rise in blood sugar concentrations. Abnormally high levels of glucose were found to affect the proliferation and differentiation processes of keratinocytes, thereby altering their function. For healing a wound, the cells surrounding the wound must survive, proliferate, migrate and grow directionally to close the wound. The signaling pathway induced by injury involves $PIP_3$ and has been shown to be essential for directional migration of corneal and skin epithelial cells, subsequently promoting wound healing.

Autophagy is another example for PIPs involvement in mediating cellular function. Autophagy, an intra-cellular process in eukaryotic cells, allows for the digestion and recycling of cytoplasmic contents through the formation of double-membrane vesicles (autophagosomes) that undergo degradation through fusion with lysosomes. Basal autophagy plays an important role in cellular homeostasis. Autophagy can also be induced as a cellular reaction to various situations, such as nutrient starvation or pathogen infection. Thus, dysfunction in autophagy has been implicated in the pathogenesis of various diseases, like cancer, infectious diseases and neurodegenerative disorders.

For example, since decrease in autophagy flux is correlated with insulin resistance of hepatocytes in obesity, it may be solved by up-regulating the autophagy flux. It has been suggested that obesity which is correlated with elevated triglycerides, free fatty acids and glucose concentrations in the plasma results in defective autophagy in the liver, which promotes elevated endoplasmic reticulum stress and impaired insulin signaling.

Since autophagy is a dynamic cellular mechanism, in which autophagosomes are being formed and degrade constantly, in order to assess the effect of the complexes on autophagy, the autophagic flux is monitored. The autophagic flux is evaluated by the difference in LC3-II (autophagosomes marker) levels between cells treated with and without bafilomycin A1 (lysosomal fusion/degradation inhibitor). Autophagy is a highly evolutionarily conserved intracellular catabolic mechanism. As such, it is a highly regulated mechanism. One of the regulators of autophagy is calcium which acts as an intracellular second messenger and controls diverse cellular functions. It has been shown that autophagy also regulates $Ca^{2+}$ mobilization. Therefore, autophagy and calcium mobilization are interrelated and can affect each other.

Autophagy is a multistep mechanism consisting of the initiation of the autophagosome membrane, elongation, maturation and fusion with lysosome for degradation. Stimulation of the vacuolar protein sorting 34 (VPS34) complex generates the local production of a pool of phosphatidylinositol-3-phosphate (PI3P), which promotes autophagosomal membrane nucleation. Since phosphatidylinositol-3-phosphate (PI3P) mediates autophagosome biogenesis through membrane deformation and elongation, it can act as an autophagy activator.

Although PIPs are attractive candidates for therapeutic purposes, such applications are challenged, inter alia, by the need to overcome permeability barriers through the plasma membrane, and by the poor stability of the PIPs. Exogenous PIPs are currently introduced into cells using permeable derivatives, or assisted by polycationic carriers such as polyamines. However, the widely-used carriers, e.g. polyethyleneimine (PEI) suffer from toxicity, poor efficiency, and low biodegradability (Fischer, 1999, Godbey, 2001).

SUMMARY OF THE INVENTION

According to one aspect, the present invention provides a complex comprising at least one phosphoinositide and at least one positively charged modified polysaccharide.

According to another aspect, the present invention provides a pharmaceutical composition comprising the complex of the invention as described above and a pharmaceutically acceptable carrier.

According to a further aspect, the present invention provides a method for treatment of a disease, disorder or condition in a subject in need thereof, comprising administering to said subject the complex of the invention as described above or the pharmaceutical composition of the invention as described above.

According to yet another aspect, the present invention provides a method for delivery of a phosphoinositide into cells, comprising contacting said cells with the complex of the invention as described above or the pharmaceutical composition of the invention as described above.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 3A-3E show cryo-TEM images of (A) PI(3,4,5)P$_3$ alone, (B) Q-starch alone or Q-starch/PI(3,4,5)P$_3$ complexes at increasing N/P ratios (C: N/P=2; D: N/P=2.5; E: N/P=3).

FIGS. 6A-6C show localization of Q-starch/PI3P complexes in HEK-293 cells. A and B: Confocal images of HEK-293 cells after 2 hours exposure to complexes at N/P=1 (A) or at N/P=2 (B); Red: WGA Alexa Fluor 555 attached to cell membranes; green—DTAF bound to Q-starch. C: ImageStream analysis of HEK-293 cell uptake after 2 hours exposure to complexes at N/P=1 or at N/P=2 showing percentage of cells with A-starch-DTAF. The percentage is 0.04 (untreated), 17.83 (N/P=1), 83.73 (N/P=2) (average of three preparations±standard deviation, n=3).

DETAILED DESCRIPTION OF THE INVENTION

Figure 1:
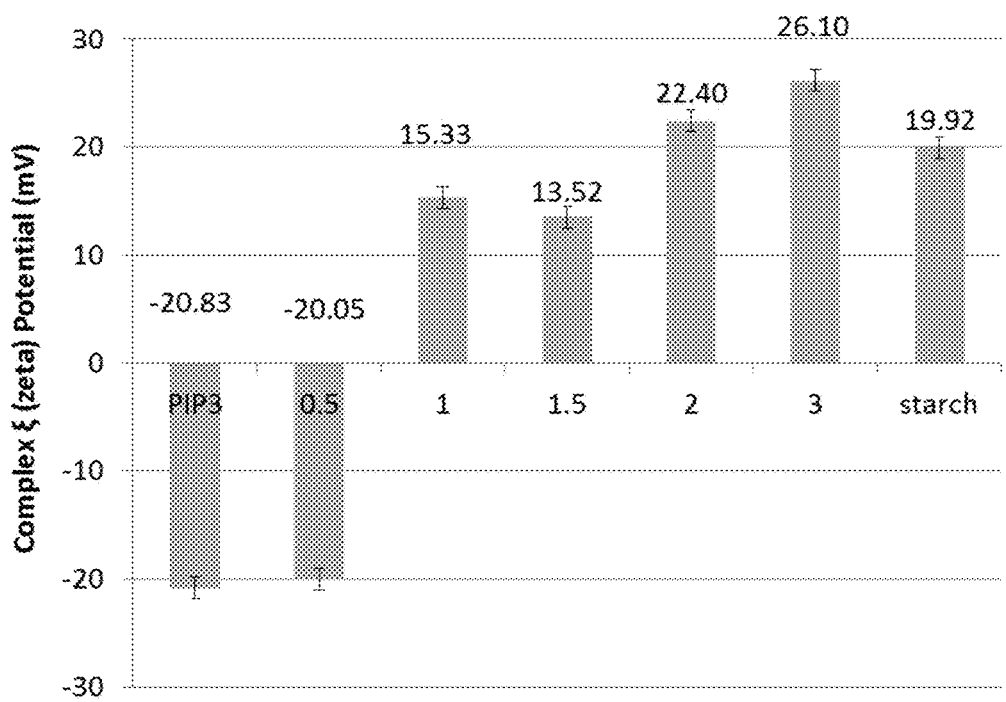
FIG. 1 shows zeta potential of Q-starch/PI(3,4,5)P$_3$ complexes at increasing N/P ratio (average of three preparations±standard deviation, n=3). Left to right: PIP$_3$ alone, complex at NP ratios of 0.5, 1, 1.5, 2, 3, and starch alone. The average zeta potentials (left to right are): −20.83, −20.05, 15.33, 13.52, 22.40, 26.10, 19.92.
Figure 2A:
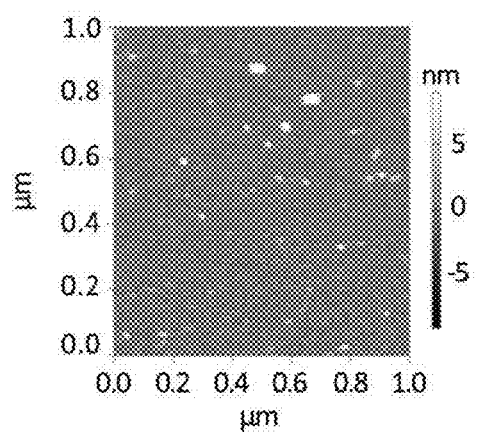
FIGS. 2A-2E show atomic force microscopy (AFM) images of (A) PI(3,4,5)P$_3$ alone, (B) Q-starch alone, or Q-starch/PI(3,4,5)P$_3$ complexes at increasing N/P ratios (C: N/P=1.5; D: N/P=2; E: N/P=3).
Figure 2B:
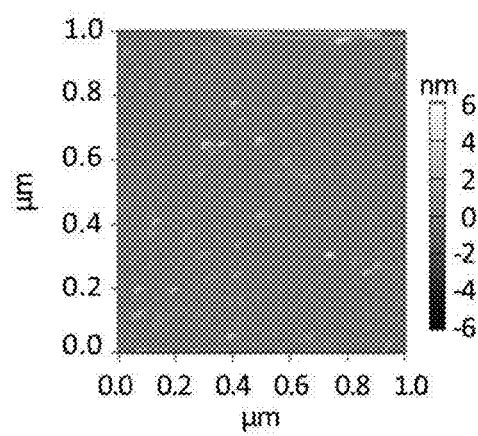
Figure 2C:
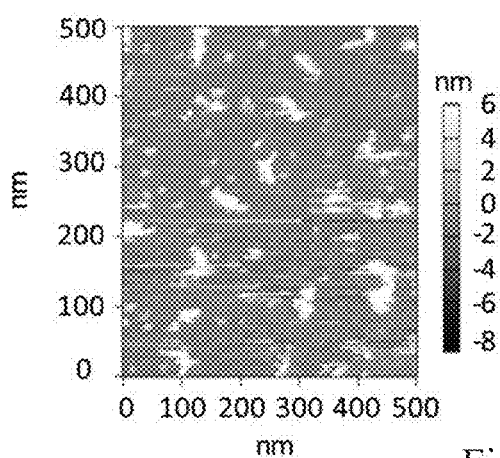
Figure 2D:
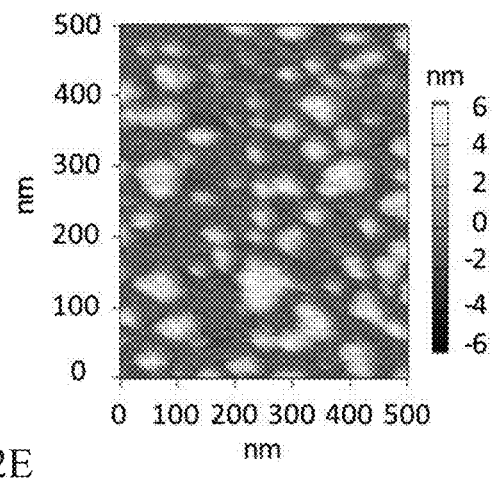
Figure 2E:
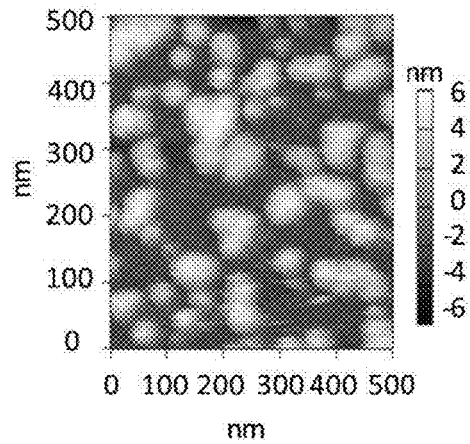

It has been found in accordance with the present invention that delivery of phosphoinositides into mammalian cells is effectively facilitated by complexation with positively charged modified polysaccharides. This approach is based on the assumption that such positively charged modified polysaccharides would be able to interact with negatively charged PIPs to generate self-assembled complexes thereby enabling PIPs entrapment. The use of polysaccharides as delivery systems is advantageous over existing carriers due to their natural characteristics such as biodegradability, biocompatibility, low immunogenicity, and minimal cytotoxicity.

Starch polysaccharide is composed of amylose (linear polymer) and amylopectin (branched polymer) with repetitive unites of glucose. The repeating units of amylose are linked by α(1-4) linkages, and the amylopectin consists of an α(1-4) linked backbone and α(1-6) linked branches. Dextrin is a group of low-molecular-weight carbohydrates produced by the hydrolysis of starch or glycogen, which is a multi-branched polysaccharide of glucose. Since starch is not cationic at physiological pH, it has to be modified in order to be an effective carrier.

Galactan is a polysaccharide made of galactose monomers, and is a component of pectin. Galactan also has to be modified to be cationic at physiological pH in order to be an effective carrier. It contains galactose chains which can serve as potential ligands for membrane receptor interaction.

Since some galectins (a family of galactose-binding lectin receptors) have increased levels in various cancers cells, they can provide a potential path for cancer therapy using modified pectic galactan (the part of pectin mainly comprising galactan), as a carrier.

Chitosan is a linear polysaccharide composed of randomly distributed β-(1-4)-linked D-glucosamine (deacetylated unit) and N-acetyl-D-glucosamine (acetylated unit) residues. Because of the deacetylated amine groups, chitosan is positively charged at physiological pH and does not necessarily need to be modified to be an effective carrier for negatively-charged molecules. However, since the positive charge of chitosan is pH dependent, it is advantageous to modify chitosan to have a permanent positive charge.

Glycosaminoglycans (GAGs) are also polysaccharides that can be used with this invention as carriers for delivery of phosphoinositides, for example chondroitin sulfate, dermatan sulfate, keratan sulfate, heparin, heparan sulfate and hyaluronan. All of these GAGs, except for hyaluronan, are sulfated and therefore have a negative charge. Therefore they should be modified to be positively charged in order be effective carriers for the negatively charged phosphoinositides.

It is appreciated that in order to be used in accordance with the invention, the modified polysaccharide must be positively charged at a physiological pH, which is between pH 7 and pH 8.

In one aspect, the present invention thus provides a complex comprising at least one phosphoinositide and at least one positively charged modified polysaccharide.

The term "modified" as used herein, refers to a polysaccharide which is substantially identical to the original polysaccharide but differing by the presence of at least a positively charged group, which can be introduced by various chemical modifications, such as esterification, etherification, oxidation, sialylation, fucosylation, sulphatation, methylation or acetylation. In the present invention, the polysaccharides were modified to become positively charged by a process of quaternization, which was carried out as described by Geresh et al., 2000.

Thus, in certain embodiments, the modified polysaccharide is a quaternized polysaccharide.

In certain embodiments, the polysaccharide is selected from the group consisting of starch, amylose, amylopectin, galactan dextrin and chitosan.

Quaternization is the process of introducing quaternary ammonium groups to a compound. In the case of polysaccharides, the hydroxyl groups of the polysaccharide are generally the site of incorporation of the ammonium groups, however, not all hydroxyl groups have the same likelihood of being modified in this method. For example, in the case of starch, the hydroxyl group at the 2' or 6' position of the glucose monomer is the most susceptible to quaternization.

Quaternization of polysaccharides can be performed by various methods, such as, e.g., those described in U.S. Pat. No. 4,031,307; Yudovin-Farber et al. (2005) Bioconjugate Chem 16:1196-1203; Houbin et al. (2004) Colloids and Surfaces A: Physiochem. Eng. Aspects 242:1-8; Huiqun et al. (2007) Carbohydrate Polymers 69:29-40; Zhishen et al. (2001) Carbohydrate Research 333:1-6; and Geresh et al., 2000.

In certain embodiments, the polysaccharide is quaternized to its full capacity. For example, fully quaternized starch has at least 3-4% nitrogen per monomeric unit, by weight. This most likely corresponds to quaternization on the 2' or 6' position on the glucose in all monomers. In certain embodiments, the quaternized starch has about 3.1% nitrogen per monomeric unit. In certain embodiments, the polysaccharide is not quaternized to its full capacity.

The degree of substitution (DS) of quaternized starch is defined by the following formula: Formula I: $DS=(162\times N\%)/(14\times 100-151.5\times N\%)$, wherein 162 is the molecular weight of anhydroglucose units (AGU) of starch, N % is the % of nitrogen estimated from elemental analysis, 151.5 is the molecular weight of 2,3-poxypropyl trimethyl ammonium chloride (the quaternization agent), and 14 is the molecular weight of nitrogen. For example, for 3% nitrogen the DS calculated according to Formula I is 0.51, and for 4% nitrogen the calculated DS is 0.82. Accordingly, in certain embodiments, the DS of the polysaccharide is about 0.51 to about 0.82.

Starches, as well as amylose or amylopectin, from various sources can be used with this invention. The major sources of starch are the cereals (rice, wheat, and maize) and the root vegetables (potatoes and cassava). Other sources may include corns, arrowroot, arracacha, bananas, barley, breadfruit, buckwheat, canna, colacasia, katakuri, kudzu, malanga, millet, oats, oca, polynesian arrowroot, sago, sorghum, sweet potatoes, rye, taro, chestnuts, water chestnuts and yarns, and many kinds of beans, such as favas, lentils, mung beans, peas, and chickpeas.

Various types of starch can be modified and used as carriers in accordance with the present invention. For example, high molecular weight (MW) starches ($10^6$ Da) from potato, corn or rice, lower MW starches ($10^4$-$10^5$ Da), and very low MW starches ($10^3$ Da), which are obtained by cleavage, such as enzymatic cleavage or cleavage by ultrasound of the starch before or after quaternization. The starches from different plant sources may also differ in their amylose/amylopectin content.

Thus, in certain embodiments, the polysaccharide is starch. In certain embodiments, the starch is selected from the group consisting of rice starch, corn starch, potato starch, and potato soluble starch. In certain embodiments, the positively charged modified polysaccharide is quaternized starch.

Potato soluble starch used with this invention is produced by degradation of potato starch by enzymatic cleavage, and it contains 20-30% amylose and 70-80% amylopectin.

Other methods for generating soluble starch also exist, for example, mechanical chain scission using ultrasound.

In certain embodiments, the molecular weight of the starch is in a range selected from the group consisting of about $10^3$ to about $10^6$ daltons, about $10^4$ to about $10^5$ daltons, and about $10^4$ to $5\times 10^4$ daltons, or the molecular weight is about 26,500 daltons.

The term "about" as used herein means that values that are 10% or less above or below the indicated values are also included.

Phosphoinositides are lipids based on phosphatidylinositol wherein the inositol ring is phosphorylated. The phosphate groups render these molecules with a negative charge at physiological pH. Phosphoinositides make up only a small fraction of cellular phospholipids, yet they control almost all aspects of a cell's life and death. They control organelle biology by regulating vesicular trafficking, but they also modulate lipid distribution and metabolism via their close relationship with lipid transfer proteins. Phosphoinositides regulate ion channels, pumps, and transporters and control both endocytic and exocytic processes. Aberrant phosphoinositide metabolism is responsible for a number of human diseases including cancer, cardiovascular diseases, neurodegenerative diseases, metabolic syndrome disorders including obesity and diabetes, infections and muscle diseases, aging, Crohn's disease and Lowe syndrome. Moreover, it is increasingly evident that a number of infectious agents hijack the phosphoinositide-dependent regulatory systems of host cells for their intracellular movements, replication, and assembly.

The inositol ring of phosphatidylinositol is phosphorylated on the three, four or five hydroxyl groups in seven different combinations, the two and six hydroxyl group is typically not phosphorylated due to steric hindrance. Phosphoinositides include: phosphatidylinositol monophosphates including phosphatidylinositol 3-phosphate (PI3P), phosphatidylinositol 4-phosphate (PI4P), and phosphatidylinositol 5-phosphate (PI5P); phosphatidylinositol bisphophosphates including phosphatidylinositol 3,4-bisphosphate ($PI(3,4)P_2$), phosphatidylinositol 3,5-bisphosphate ($PI(3,5)P_2$), and phosphatidylinositol 4,5-bisphosphate ($PI(4,5)P_2$); and phosphatidylinositol 3,4,5-trisphosphate ($PI(3,4,5)P_3$ also often referred to as $PIP_3$).

As can be seen from Example 3, complexes of Q-starch with PI3P are internalized by HEK-293 cells, and as seen from Example 4, incubation of cells with these complexes caused up-regulation of autophagy. Additionally, it is known that PI4P and PI5P up-regulate autophagy similar to PI3P (Yamashita, 2007, Vicinanza, 2015), that $PI(4,5)P_2$ can help improve insulin resistance and wound healing (Strawbridge, 2005), that $PI(3,5)P_2$ levels are elevated in response to cellular stress (Stephen, 1997), and that $PIP_3$, production of which is induced by insulin, has been shown to constitute a major lipid messenger in insulin-mediated metabolic actions in muscle and fat (Ishiki et al., 2005, Sweeney et al., 2004, Patel at al., 2003, Jiang et al., 1998, Payrastre B., et al, 2001).

Therefore, according to some embodiments, the phosphoinositide is selected from the group consisting of phosphatidylinositol 3-phosphate (PI3P), phosphatidylinositol 4-phosphate (PI4P) phosphatidylinositol 5-phosphate (PI5P), phosphatidylinositol 3,4-bisphosphate ($PI(3,4)P_2$), phosphatidylinositol 3,5-bisphosphate ($PI(3,5)P_2$), phosphatidylinositol 4,5-bisphosphate ($PI(4,5)P_2$), and phosphatidylinositol 3,4,5-trisphosphate ($PI(3,4,5)P_3$ or $PIP_3$).

According to some embodiments, the phosphoinositide is phosphoinositide 3-phosphate or phosphatidylinositol 3,4,5-trisphosphate.

The shape and size of the phosphoinositide-modified polysaccharide complexes are important, inter alia, in the internalization process. The molecular weight of the carrier and the molar ratio of positively charged amine groups on the polysaccharide to negatively charged phosphates on the phosphoinositide (termed herein "N/P ratio") affect the shape and size of the complex, because the interaction between the positively charged polysaccharides and the negatively charged phosphoinositide causes the complex to condense into compact, ordered particles.

Thus, in certain embodiments, the molar ratio of positively charged amine groups on the positively charged polysaccharide to negatively charged phosphates on the phosphoinositide, i.e. the N/P ratio, is in a range selected from the group consisting of about 0.1-100 and about 0.5-10, or the ratio is about 2.

As can be seen from Examples 1 and 2, the size of the complex varies, depending on the N/P ratio and the identity of the phosphoinositide, and the hydrodynamic radius is between 10 and 500 nm, between 20 and 300 nm or between 50 and 180 nm.

Thus, in certain embodiments, the complex of the invention is in the form of a nanoparticle.

Some obstacles to successful delivery may include induction of an immune response, cytotoxicity to healthy cells, and difficulty in achieving an effective concentration of the drug at the site to be treated, and therefore it is advantageous to direct the drug to the target cells, thereby enabling more effective treatment with fewer side effects. This can be achieved, inter alia, by adding targeting moieties such as ligands or antibodies to the delivery system to mediate binding and internalization by receptors on the surface of target cells.

Examples for ligands that can be used for targeting of the phosphoinositide-polysaccharide complex to cells or tissues of interest include, for example peptides containing RGD sequence for binding to specific integrin receptors, growth factor receptors ligands such as EGF and TGFα, or antibodies or antibody mimetics, such as affibodies, to tumor-associated antigens.

In certain embodiments, the complex further comprises a targeting ligand.

Additionally, further moieties may be used with the complexes of the invention, for example polyethylene glycol (PEG) for stabilization of the complex and protection from enzymatic degradation.

The complexes of the invention may be used for treating diseases, disorders or conditions in a subject. Such diseases, disorders or conditions include, for example, diseases, disorders or conditions involving autophagy, such as, fatty liver, obesity, cancer (e.g. breast cancer, myeloma, glioblastoma), neurodegenerative disorders, and infectious diseases such as Hepatitis C; diseases, disorders or conditions involving insulin resistance and/or aberrant wound healing such as diabetes; diseases, disorders or conditions which can be treated by enhancing cell migration, particularly skin cell migration, such as skin damage due to injury, wounds, aging, or diabetes; and additional diseases or disorders including cardiovascular diseases, metabolic syndrome disorders such as obesity (and diabetes), infections and muscle diseases and aging. As explained below, the complexes of the invention may additionally be used for enhancing migration of cells, particularly of skin cells, such as for skin rejuvenation or repair.

The diseases, disorders or conditions may be associated with impaired phosphoinositide-mediated signaling.

PI3P is known to be an autophagy activator, and as can be seen from Examples 4 and 5, complexes including PI3P succeeded in triggering calcium mobilization and up-regulating autophagy flux. Accordingly, complexes including PI3P may be used for treating diseases related to autophagy, such as cancer, infectious diseases, and neurodegenerative disorders. Additionally, decrease in autophagy flux is correlated with insulin resistance of hepatocytes in obesity, and therefore obesity and hepatic insulin resistance may also be treated by PI3P. Since PI4P and PI5P are known to regulate autophagy similar to PI3P, complexes including PI4P and PI5P may also be used for the same treatments.

$PIP_3$ was shown to be essential for directional migration of corneal and skin epithelial cells and therefore may be used for promoting wound healing.

More generally, as a result of its involvement in migration of cells, $PIP_3$ facilitates the healing, rejuvenation, and repair of tissues, primarily skin tissues, which sustain damage from injuries, wounds, or due to aging.

It follows that the complexes of the invention which include $PIP_3$ may be used in products including dermal and sub-dermal fillers for aesthetic applications, topical ointments for post-surgery skin treatment, and scar healing ointments that facilitate the healing, rejuvenation, and repair of tissues primarily skin tissues, following damage from injuries, wounds, or due to aging or other conditions which affect skin integrity.

Additionally, since $PIP_3$ has been shown to constitute a major lipid messenger in insulin-mediated metabolic actions in muscle and fat, it may be used for treating diabetes and obesity.

Accordingly, the present invention provides a pharmaceutical composition comprising the complex of the invention and a pharmaceutically acceptable carrier.

Methodology and components for formulation of pharmaceutical compositions are well known and can be found, for example, in Remington's Pharmaceutical Sciences, Eighteenth Edition, A. R. Gennaro, Ed., Mack Publishing Co. Easton Pa., 1990. Pharmaceutical compositions for use in accordance with the present invention thus may be formulated in conventional manner using one or more physiologically acceptable carriers comprising excipients and auxiliaries, which facilitate processing of the active agents into preparations that can be used pharmaceutically. Proper formulation is dependent upon the route of administration chosen.

The term "pharmaceutically acceptable carrier" refers to a vehicle which delivers the active components to the intended target and which will not cause harm to humans or other recipient organisms. As used herein, "pharmaceutical" will be understood to encompass both human and veterinary pharmaceuticals. Useful carriers include, for example, water, acetone, ethanol, ethylene glycol, propylene glycol, butane-1, 3-diol, isopropyl myristate, isopropyl palmitate, mineral oil and polymers composed of chemical substances like polyglycolic acid or polyhydroxybutyrate or natural polymers like collagen, fibrin or polysaccharides like chitosan and alginate. The carrier may be in any form appropriate to the mode of delivery, for example, solutions, colloidal dispersions, emulsions (oil-in-water or water-in-oil), suspensions, creams, lotions, gels, foams, mousses, sprays and the like.

In another aspect, the present invention provides a method for treatment of a disease, disorder or condition in a subject in need thereof, comprising administering to said subject the complex of the invention as described above, or the pharmaceutical composition of the invention as described above.

In some embodiments, the disease disorder or condition is associated with impaired phosphoinositide-mediated signaling.

In some embodiments, the disease disorder or condition is selected from the group consisting of diseases disorders or conditions associated with autophagy such as fatty liver, obesity, cancer, infectious diseases, and neurodegenerative disorders; diseases disorders or conditions associated with insulin resistance and/or with aberrant wound healing; diseases, disorders or conditions which can be treated by enhancing cell migration, particularly skin cell migration, such as skin damage due to injury, wounds, aging, or diabetes; and additional diseases including cardiovascular diseases, metabolic syndrome disorders such as obesity, infections and muscle diseases, aging, Crohn's disease and Lowe syndrome.

In some embodiments, the phosphoinositide is selected from the group consisting of phosphatidylinositol 3-phosphate, phosphatidylinositol 4-phosphate, and phosphatidylinositol 5-phosphate, and the disease disorder or condition is selected from the group consisting of diseases disorders or conditions associated with autophagy and/or with insulin resistance such as fatty liver, obesity, cancer, infectious diseases, and neurodegenerative disorders.

In some embodiments, the phosphoinositide is phosphatidylinositol 3-phosphate and the disease disorder or condition is selected from the group consisting of diseases disorders or conditions associated with autophagy and/or with insulin resistance such as fatty liver, obesity, cancer, infectious diseases, and neurodegenerative disorders.

In some embodiments, the phosphoinositide is selected from the group consisting of phosphatidylinositol 3,4,5-trisphosphate and phosphatidylinositol,4,5-disphosphate, and the diseases, disorder or condition is selected from the group consisting of diseases disorders or conditions associated with insulin resistance and/or with aberrant wound healing; and diseases, disorders or conditions which can be treated by enhancing cell migration, particularly skin cell migration, such as skin damage due to injury, wounds, aging, or diabetes.

In some embodiments, the phosphoinositide is phosphatidylinositol 3,4,5-trisphosphate and the diseases, disorder or condition is selected from the group consisting of diseases disorders or conditions associated with insulin resistance and/or with aberrant wound healing; and diseases, disorders or conditions which can be treated by enhancing cell migration, particularly skin cell migration, such as skin damage due to injury, wounds, aging, or diabetes.

The term "treating" or "treatment" as used herein includes alleviating, abrogating, substantially inhibiting, slowing, reducing or reversing the progression of a condition, substantially ameliorating or reducing clinical symptoms of a condition, substantially preventing the appearance of clinical symptoms of a condition, or complete cure of the disease. With regard to cancer, the term refers to preventing or delaying cancer recurrence, inhibiting tumor growth or causing death of cancer cells. Such treatment can also lead to regression of tumor growth, i.e., to decrease in size or complete regression of the tumor, and to elimination of metastases. The terms "tumor" and "cancer" are used interchangeably herein.

The term "tumor" as used herein refers to an abnormal mass of tissue, the growth of which exceeds and is uncoordinated with that of the normal tissues, and persists in the same excessive manner after cessation of the stimulus which evoked the change. Normal cells, if they propagate, do so in a controlled manner. This term also refers to metastases i.e. secondary cancerous growth formed by transmission of cancerous cells from a primary growth located elsewhere in the body.

The composition of the invention can be administered in a variety of ways. The routes of administration include, but are not limited to, intratumoral, intraliver, intradermal, transdermal (e.g. in slow release formulations), intramuscular, intraperitoneal, intravenous, intracoronary, subcutaneous, oral, epidural, intraocular, auricular (otic), intrauterine extraamniotic, vaginal, topical, and intranasal routes. The composition of the invention can be administered also as eyedrops or ear-drops. Any other therapeutically efficacious route of administration can be used.

For injection, the active ingredients of the compositions of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

For oral administration, the compositions can be formulated readily by combining with pharmaceutically acceptable carriers well known in the art. Such carriers enable the compositions of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The compositions of the present invention may also be formulated in rectal compositions such as suppositories or retention enemas, using, e.g., conventional suppository bases such as cocoa butter or other glycerides.

The compositions of this invention can also be administered topically to a subject, e.g., by the direct laying on or spreading of the composition on the epidermal or epithelial tissue of the subject, or transdermally via a "patch". Such compositions include, for example, ointments, lotions, creams, solutions, gels and solids, with or without chemical enhancers, which are substances used for affecting penetration or permeation of drugs. Chemical penetration enhancers (CPEs) can increase permeability by acting as solvents dissolving lipids or denaturing skin proteins. In other cases, CPEs can modify drug solubility in the skin thus increasing drug penetration. Examples for CPEs include alcohols, amines and amides, urea, amino acids and their esters, fatty acids and their esters, macrocyclic compounds, sulfoxides, and tensides.

Pharmaceutical compositions suitable for use in context of the present invention include compositions wherein the active ingredients are contained in an amount effective to achieve the intended purpose. More specifically, a "therapeutically effective amount" means an amount of an active ingredient effective to prevent, alleviate or ameliorate symptoms of a disease or disorder or prolong the survival of the subject being treated.

Determination of a therapeutically effective amount is well within the capability of those skilled in the art, especially in light of the detailed disclosure provided herein.

Depending on the severity and responsiveness of the condition to be treated, dosing can be of a single or a plurality of administrations or a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

In yet another aspect, the present application provides a method for delivery of a phosphoinositide into cells, comprising contacting said cells with the complex of the invention as described above.

In certain embodiments, the cells are mammalian cells, such as muscle cells, liver cells, fat cells, macrophages, keratinocytes, or stem cells.

The term "contacting" as used herein relates to physical contact of the complexes and the target cells. The contacting can be direct, i.e. directly applying the complexes to the target cells, such as when applying a solution of complexes to cells in culture or by topical administration to the skin when the target cells are skin cells of the outer layer, or it can be indirect, such as when applying the complexes to the outer layer of the skin when the target cells are keratinocytes in the basal layer, when applying the complexes to the blood stream by intravenous administration when the target cells are tumor cells of an internal organ, or in other uses when the complexes are not applied directly to the target cells, such as applying the complexes to a membrane, such as to the eardrum (tympanic membrane), amniotic sac, the eye, or by an intratumoral, subcutaneous or intramuscular injection.

EXAMPLES

Experimental
Materials Used:
Soluble potato starch (101252) was purchased from Merck. 3-Chloro-2hydroxypropyltrimethylammonium chloride (348287), Dialysis cellulose membrane (D9652), Phosphate buffered saline (PBS) (P4417) and 3-Methyladenine (3-MA) (M9281) were purchased from Sigma-Aldrich Inc. Phosphatidylinositol 3-phosphate diC8 (P-3008), phosphatidylinositol (3,4,5) trisphosphate diC16 (P-3916) and Carrier 3 (P-9C3) 50 nmoles were purchased from Echelon Biosciences Incorporated Salt Lake City, Utah. Dulbecco s Modified Eagle Medium (DMEM) with 4.5 g/l D-Glucose (High Glucose) (01-055-1) Fetal Bovine Serum (FBS) (04-121-1A), Trypsin Ethylenediaminetetraacetic acid (EDTA) (03-052-1B), L-glutamine (03-020-1B), Penicillin-streptomycin (03-031-1B), Earle's Balanced Salt Solution (EBSS) (02-010-1A) were purchased from Biological Industries Beit Haemek. The Vacuolar $H^+$ ATPase inhibitor-bafilomycin A1 was provided by Assaf Rudich.

Starch Quaternization:
Starch modification with quaternary amine groups to obtain quaternized starch (Q-starch) was carried out according to Geresh et ah, 2000). Briefly, 500 mg of soluble potato starch (hydrolyzed potato starch, Mw 26,765 Da, Sieradzki et ah, 2008) were dissolved in sodium hydroxide solution (0.19 g/ml) to obtain 50 mg/ml starch concentration. The solution was then stirred continuously for 30 min at room temperature. 9 g (7.8 ml) of the quaternization reagent, 3-Chloro-2hydroxypropyltrimethylammonium chloride (CHMAC), were dissolved in distilled water (DW) (0.45 g/ml) and added to the starch solution. The reaction volume was continuously stirred for 20 h at room temperature. One volume of product was precipitated by adding 4 volumes of acidified (1% HCl) mixture of ethanol and acetone (1:3 vol.). The precipitate was washed 4 times with 25 ml of ethanol 80%, dissolved in a small volume (1-2 mL) of DW and poured into an 11 kDa cutoff dialysis bag that was placed in a vessel containing 5 L of DW. The water was replaced 4 times with fresh DW during 48 hr of dialysis. The dialyzed product was then dried by lyophilization.

Chemical Analysis of Quaternized Starch:

Quaternization of the starch was confirmed by $^1$H NMR spectroscopy with a 500 MHz Brucker spectrometer. NMR of the quaternization reagent and quaternized starch was done in $D_2O$ solvent and NMR of native starch was done in DMSO solvent. The nitrogen content (% N weight) of Q-starch was measured by the Kjeldahl method (Vogel, A. I., A textbook of quantitative inorganic analysis, Longman, London, 1961, pp. 256-257).

Q-Starch/PIP$_3$ Complex Preparation:

Complexes of Q-starch and PIP$_3$ were prepared at various N/P molar ratios (molar ratio between positive nitrogen groups on Q-starch and negative phosphate groups on the PIP). Q-starch dissolved in double distilled water (DDW) was added in aliquots to sonicated solutions containing PIP (amounts determined by the desired N/P ratio). Following gentle vortexing, the samples were incubated at room temperature for 40 min before use for complex formation through self-assembly.

Q-Starch/PI3P Complex Preparation:

Complexes of Q-starch and PI3P were prepared at various N/P molar ratios. The complexes were prepared by two different methods—without or with sonication and filtration of the PI3P solution prior complexation. For the first, Q-starch dissolved in double distilled water (DDW) was added in aliquots to solutions containing PIP (amounts determined by the desired N/P ratio). Following gentle vortexing, the samples were incubated at room temperature for 40 min before use for complex formation through self-assembly. For the second, the PI3P solutions were sonicated and filtered through 0.45 μm filter PVDF membrane before adding the Q-starch. This method of preparation enables characterization of the complexes with light scattering techniques.

The sonication was used in order to disassemble structures that the PI3P forms at concentrations above its CMC (critical micelle concentration). The filtration was used to remove unidentified accumulations in the PI3P solutions. It should be notable that since the PI3P solutions were filtered prior to complexation, and probably there was material loss to the filter, it is not possible to know the exact concentration of the PI3P solutions, therefore to determine the N/P ratio. Complexes prepared in that method are labeled with + in FIG. 5.

Complex Characterization:

The Q-starch/PI3P and Q-starch/PI(3,4,5)P$_3$ complexes were characterized using the methods below.

Dynamic Light Scattering (DLS) & Zeta Potential:

The hydrodynamic size of the complexes was measured by dynamic light scattering (DLS). Spectra were collected by using CGS-3, (ALV, Langen, Germany). The laser power was 20 mW at the He—Ne laser line (632.8 nm). Correlograms were calculated by ALV/LSE 5003 correlator, which were collected at 90°, during 20 s for 10 times, at 25° C. The correlograms were fitted with version of the program CONTIN (provencher, 1982). Samples of complexes were each diluted to a final volume of 1 mL in DDW. Each sample was measured three times and solutions were further diluted until results were independent of dilution rate. Complexes' size is presented as average of triplicates. Samples from DLS were transferred to U-tube cuvette (DTS 1070, Malvern) for subsequent zeta potential measurements using Zetasizer (ZN-NanoSizer, Malvern, England). Each sample was measured at automatic mode, at 25° C. and the Smoluchowski model was used to calculate the zeta potential. For each sample the zeta potential value was presented as the average value of three runs, and the average value of each N/P ratio is presented as the average of triplicates.

Atomic Force Microscopy (AFM):

Complex size and geometry were visualized by atomic force microscope. Before imaging, 7 μL of each sample was dispensed onto individual freshly cleaved mica surface. The 512×512 pixel images were taken in tapping mode with a scan size of up to 5 μm at a scan rate of 1 Hz.

Cryo-Transmitting Electron Microscopy (Cryo-TEM):

Complex size and geometry in solution were visualized using Cryo-TEM. TEM at cryogenic temperature (Cryo-TEM) is used for direct imaging of solutions and dispersions. Vitrified specimens are prepared on a copper grid coated with a perforated lacy carbon 300 mesh (Ted Pella Inc.). A typically 4 μl drop from the solution is applied to the grid and blotted with a filter paper to form a thin liquid film of solution. The blotted sample are immediately plunged into liquid ethane at its freezing point (−183° C.). The procedure is performed automatically in the Plunger (Lieca EM GP). The vitrified specimens are transferred into liquid nitrogen for storage. the samples are studied using a FEI Tecnai 12 G2 TEM, at 120 kV with a Gatan cryo-holder maintained at −180° C., and images are recorded on a slow scan cooled charge-coupled device CCD camera Gatan manufacturer. Images are recorded with the Digital Micrograph software package, at low dose conditions, to minimize electron beam radiation damage.

Autophagy Flux:

Autophagy Flux was assessed using western blot by comparing of the cumulative LC3-II levels in HEK293 cells with and without autophagy inhibitor—bafilomycin A1 (vacuolar H+ ATPase inhibitor, 0.1 μM). Bafilomycin A1 inhibits autophagosomes degradation by fusion with lysosome since it prevents the lysosome acidification. LC3-II is an autophagosomal membrane protein therefore it is used as autophagy marker. HEK293 cells were seeded in a 6-well plate 24 hours before treatment in DMEM growth media. The cells were incubated with or without bafilomycin A1 and 3-Methyladenine (3-MA) in EBSS for 2 hours (3-MA, 5 mM) in 37° C. and 5% $CO_2$. 3-MA acts as an autophagy inhibitor since it inhibits III phosphatidylinositol 3-kinases (PI-3K) which produce the endogenous PI3P. At the second hour the cells were treated with Q-starch/PI3P complexes at N/P ratio of 2 and with PI3P alone as control (final PI3P concentration in each well was 0.5 μM).

Example 1: Q-Starch/PI(3,4,5)P$_3$ Complex Characterization

The zeta potentials of the Q-starch/PIP$_3$ complexes are shown in FIG. 1 for N/P ratios of 0.5 to 3 and for the PIP$_3$ and Q-starch alone. As seen in FIG. 1, the zeta potential increase with increasing N/P ratio. Increasing N/P ratio increases the concentration of the positively charged nitrogen groups on the Q-starch until the carrier/PIP$_3$ complexes has a net positive surface charge. According to the Zeta potential results, any complex with a N/P ratio above 1 is positively charged and can be used. The AFM images of the Q-starch/PIP$_3$ complexes are shown in FIG. 2 for N/P ratios of 1.5 to 3 and for the PIP$_3$ and Q-starch alone. As seen in FIG. 2, increasing the N/P ratio changes the shape and amount of the particles. The cryo-TEM images of the Q-starch/PIP$_3$ complexes are shown in FIG. 3 for N/P ratios of 2 to 3 and for the PIP$_3$ and Q-starch alone. As seen in FIG. 3 PIP$_3$ alone has the shape of long filaments, starch demonstrates an empty grid and the complexes look like particles. Also it can be seen that only at N/P=3 there is no isolated PIP$_3$ in the sample, and the sample contains only complexes.

The mean hydrodynamic radius for Q-starch/PIP$_3$ complexes were about 121 nm for N/P=1.5; about 84 nm for N/P=2; about 51 nm for N/P=2.5 and about 44 nm for N/P=3 (data not shown).

Example 2: Q-Starch/PI3P Complex Characterization

Figure 4A:
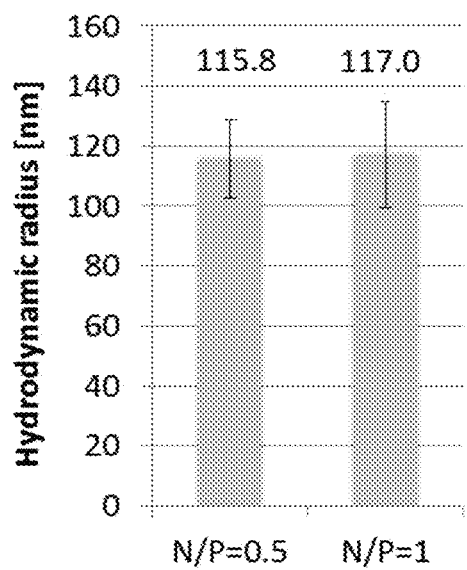
FIGS. 4A-4B show characterization of Q-starch/PI3P complexes (prepared without sonication and filtration of the PI3P solution prior to complexation) at increasing N/P ratios. A: Hydrodynamic radius of complexes at various N/P ratios. Average hydrodynamic radius was (left to right): 115.8±13.0 (N/P=0.5) and 117.0±17.7 (N/P=1) (average of three preparations±standard deviation, n=3). B: Zeta potential of Q-starch/PI3P complexes at increasing N/P ratio. Left to right: 0.5 μM PI3P alone, complexes at N/P ratios of 0.5 and 1, and 0.45 mg/L Q-starch alone. The average zeta potentials (left to right are): −14.8±3.8, −3.4±0.1, −0.5±0.1, 10.8±2.9. (average of two preparations for N/P=0.5 and one preparation for N/P=1±standard deviation, n=3).
Figure 4B:
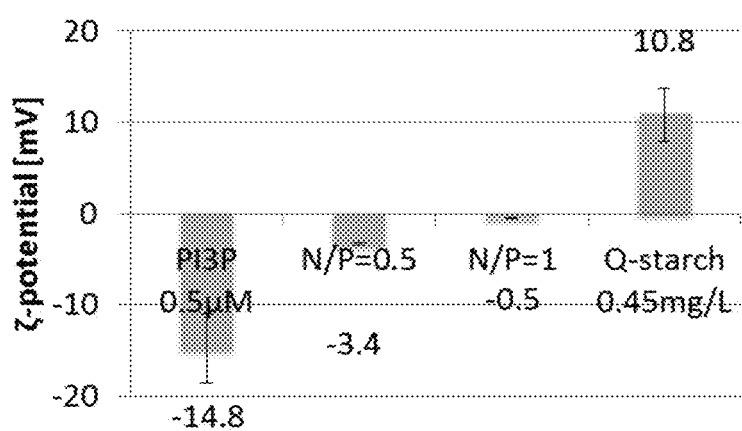
Figure 5A:
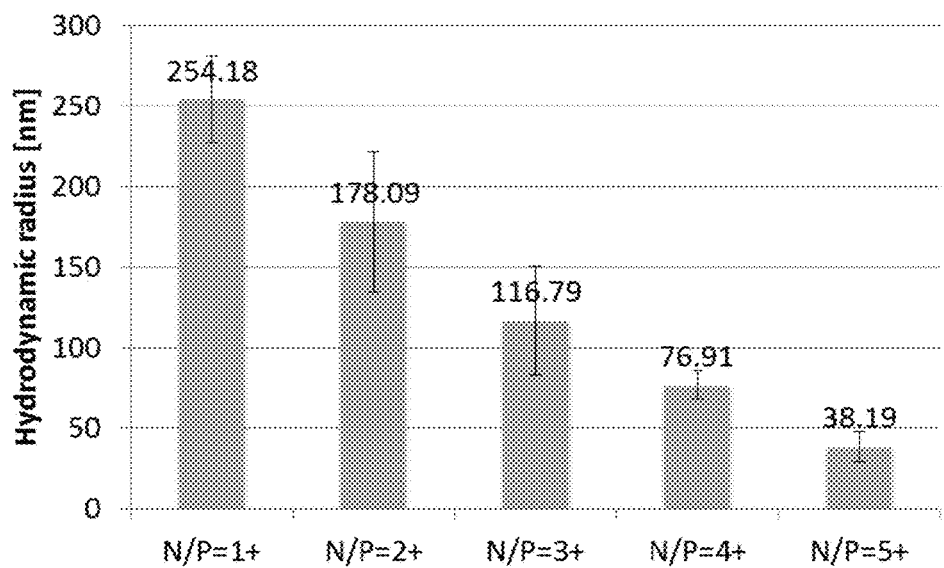
FIGS. 5A-5B show characterization of Q-starch/PI3P complexes (prepared with sonication and filtration of the PI3P solutions prior complexation) at increasing N/P ratios. A: Hydrodynamic radius of Q-starch/PI3P complexes at increasing N/P ratios (average of three preparations±standard deviation, n=3). Average hydrodynamic radius (left to right): 254.18 (N/P=1), 178.09 (N/P=2), 116.79 (N/P=3), 76.91 (N/P=4), and 38.19 (N/P=5) (average of three preparations±standard deviation, n=3). B: Zeta potential of Q-starch/PI3P complexes at increasing N/P ratios. The average zeta potentials (left to right are): −10.1 (N/P=1), −3.0 (N/P=2), 5.4 (N/P=3), 7.9 (N/P=4), 11.9 (N/P=5) (average of three preparations±standard deviation, n=3).
Figure 5B:
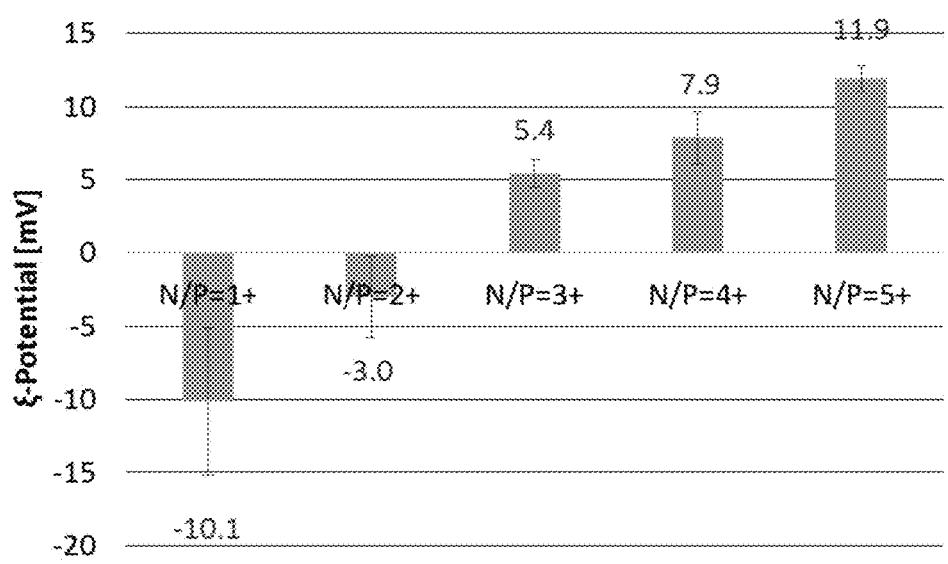

The hydrodynamic radius of the Q-starch/PI3P complexes without sonication and filtration of the PI3P solution prior complexation is shown in FIG. 4A for N/P ratios of 0.5 and 1. As seen in FIG. 4A, the mean hydrodynamic radius of self-assembled Q-starch/PI3P complexes, as measured by Dynamic Light Scattering (DLS), is approximately 116 nm. The zeta potentials of these complexes are shown in FIG. 4B for N/P ratios of 0.5 and 1 and for PI3P and Q-starch alone. As seen in FIG. 4B, the zeta potential increases with increasing the N/P ratio. The hydrodynamic radius of the Q-starch/PI3P complexes prepared with sonication and filtration of the PI3P solution prior complexation is shown in FIG. 5A for N/P ratios of 1 to 5. As seen in FIG. 5A, the hydrodynamic radius of self-assembled Q-starch/PI3P complexes, as measured by Dynamic Light Scattering (DLS), inversely depends on the N/P ratio (between 254.18 nm at N/P=1 and 38.19 nm at N/P=5). The zeta potentials of these complexes are shown in FIG. 5B for N/P ratios of 1 to 5. As seen in FIG. 5B, the zeta potential increase with increasing the N/P ratio.

Example 3: Cellular Localization of Q-Starch/PI3P Complexes

Cellular uptake of Q-starch$^{5-DTAF}$/PI3P complexes (DTAF-5-(4,6-Dichlorotriazinyl) Aminofluorescein, a reactive green dye) was visualized using spinning disk confocal microscope. HEK-293 cells were seeded in 6-well culture plates on coverslips and incubated over-night at 37° C. with 5% CO$_2$. Then the cells were supplemented with 25 µL of Q-starch$^{5-DTAF}$/PI3P complexes solution (all diluted to $C_{PI3P}$=0.5 µM in DMEM). Afterwards the cells were incubated for 2 hours t 37° C. with 5% CO2. The cells were fixed with 4% paraformaldehyde. Cell membrane was labeled by WGA Alexa Fluor 555.

Imaging experiments using an imaging flow cytometer (Amnis ImageStreamX) were performed to quantitatively evaluate the cellular internalization of Q-starch$^{5-DTAF}$/PI3P complexes. HEK-293 cells were seeded in 6-well culture plates and incubated over-night at 37° C. with 5% CO$_2$. Then the cells were supplemented with 25 µL of Q-starch$^{5-DTAF}$/PI3P complexes solution (all diluted to $C_{PI3P}$=0.5 µM in DMEM). Afterwards the cells were incubated for 2 hours in 37° C. and 5% CO$_2$. The cells were washed once with DMEM, trypsinized, resuspended in culture medium and centrifuged at 1800 rpm for 8 min). The collected cells were then resuspended in FACS buffer and were analyzed using ImageStreamX Mark II (Amnis, Seattle, Wash.). Cell acquisition and analysis were performed using IDEAS Application, version 5.0.

As can be seen in FIGS. 6A-6C, Q-starch/PI3P complexes at N/P ratio of 2 are taken up by the cells and therefore have the suitable characteristics (size and zeta potential) that enable cellular uptake. Although these complexes have not been characterized (as explained above in the method describing preparation of the complexes with sonication), it is estimated, based on the results presented in FIG. 5, that they are in the nanometric size and have a positive zeta potential. As shown in FIGS. 4B and 5B, the zeta potential increases with increasing N/P ratio. As shown in FIG. 5A, increasing N/P ratio leads to decrease in the hydrodynamic radius.

Example 4: Autophagy Flux

Figure 7A:
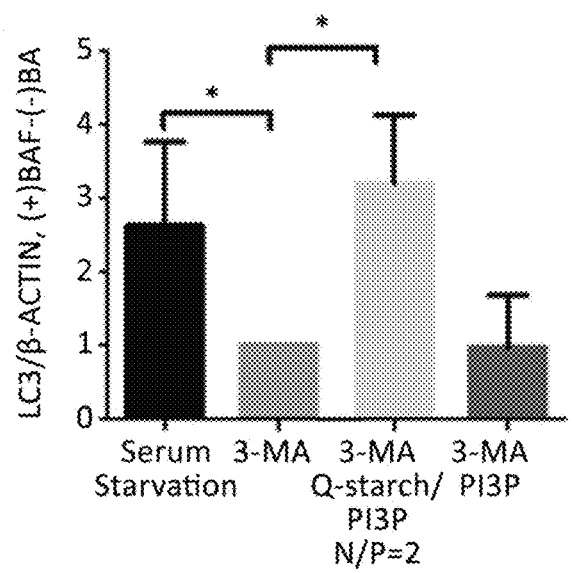
FIGS. 7A-7B show autophagy flux expressed by the difference in LC3-II levels between treatments with and without bafilomycin A1 (Baf). A: analysis of a western blot for LC3-II and β-actin antigens. Left to right treatments: serum starvation, 3-MA (3-Methyladenine), 3-MA Q-starch/ PI3P at N/P=2, and 3-MA PI3P alone. B: representative blots of the protein extracts after the indicated treatments, after running in acrylamide gel followed by LC3-II and β-actin antigens staining (n=4, *<0.05). Con: control.
Figure 7B:
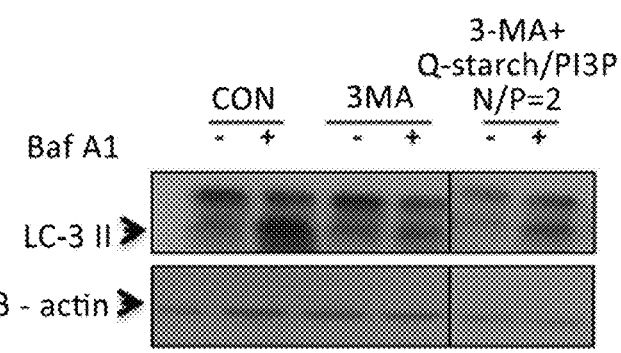
Figure 7B:
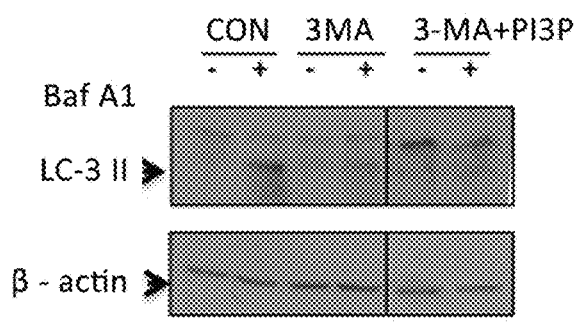

Up-regulation of autophagy in HEK293 cells with the Q-starch/PI3P complexes was assessed by comparing the autophagy flux for the following conditions (FIG. 7): flux after 3 hours of serum starvation, flux after inhibition of the formation of endogenous PI3P by 3-MA (3-Methyladenine), flux after treatment with 3-MA and complexes at N/P ratio of 2 and flux after treatment with 3-MA and PI3P. As can be seen in FIGS. 7A-7B, inhibiting endogenous PI3P formation leads to a decrease in the autophagy flux compared to serum starvation. Treatment with Q-starch/PI3P complexes at N/P=2 succeeds to up-regulate autophagy flux even when compared to serum starvation levels. Treatment with PI3P alone did not affect the levels of autophagy flux compared to treatment with 3-MA.

Example 5: The Effect of Q-Starch/PI3P on Calcium Mobilization

Calcium ions (Ca$^{2+}$) act as an intracellular second messenger and controls diverse cellular functions. Ca$^{2+}$ signaling regulates autophagy, and it has been shown that autophagy also regulates Ca$^{2+}$ mobilization. Therefore, autophagy and calcium mobilization are interrelated and can affect each other.

The effect of Q-starch/PI3P complexes on intracellular Ca$^{2+}$ stores mobilization was assessed using the fluorescent indicator Fura-2. For [Ca$^{2+}$]i (intracellular calcium) measurements, HEK 293 cells were incubated for 30 min with 2.5 µM Fura-2, in Ringer's solution with 0.1% BSA. Following dye loading, the cells were washed using Ringer's solution, and Q-starch/PI3P complexes at N/P ratios of 1 or 2 were applied (prepared from 1 mM and 0.1 g/L PI3P and Q-starch stock solution, respectively). Commercial carrier complexes, non-complexed PI3P and non-complexed Q-starch (0.9 mg/L, corresponding concentration for N/P=2) were also applied. Fura-2 was excited at 340 nm and 380 nm and imaged with a 510 nm long-pass filter. The imaging system consisted of an Axiovert 100 inverted microscope (Zeiss), Polychrome V monochromator (TILL Photonics, Germany) and a SensiCam cooled charge-coupled device (PCO, Germany). Fluorescent imaging measurements were acquired using Imaging Workbench 5 (Indec, CA).

Figure 8:
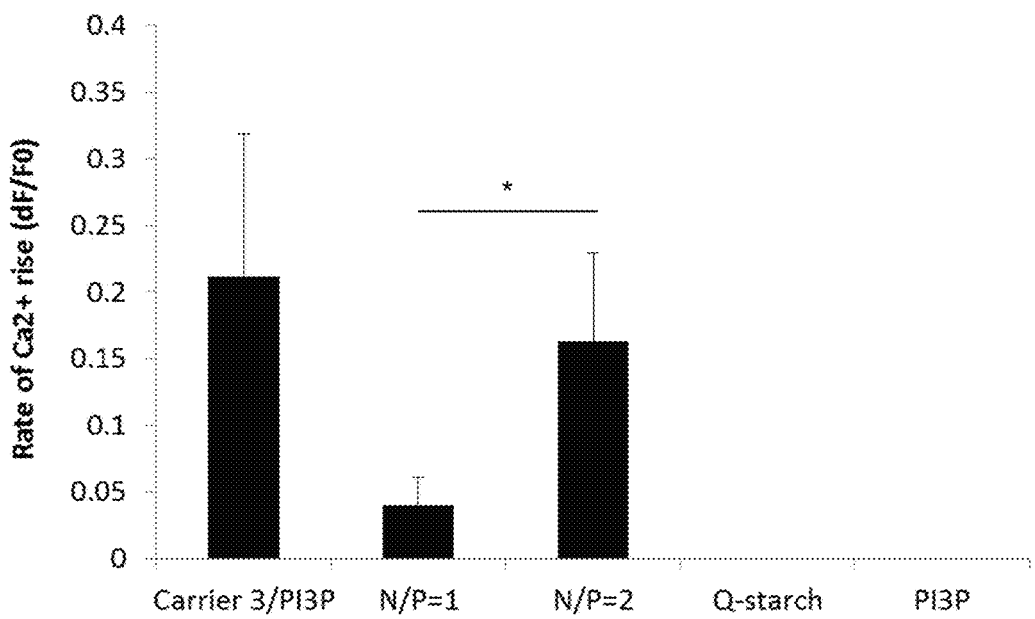
FIG. 8 shows Average rate of Ca$^{2+}$ rise (dF/F$_0$) in HEK 293 cells loaded with Fura-2, after application of (left to right): Carrier 3 (P-9C3)/PI3P complexes (n=10), Q-starch/ PI3P complexes at N/P=1 ratio (n=12), and at N/P=2 ratio (n=7), non-complexed Q-starch (n=3, 0.9 mg/L, corresponding concentration to N/P=2), and PI3P (n=2). Results are presented as mean±SEM (~30 cells per sample), *P<0.05. Fura-2 was excited at 340 nm and 380 nm and imaged with a 510 nm long-pass filter (emission wavelength). F is the fluorescence ratio (340/380) obtained from selected cells imaged with a 510 nm long-pass filter. dF/F$_0$ represents the average rate of Ca$^{2+}$ rise, F$_0$ is the fluorescence at the beginning of the experiment.
Figure 9:
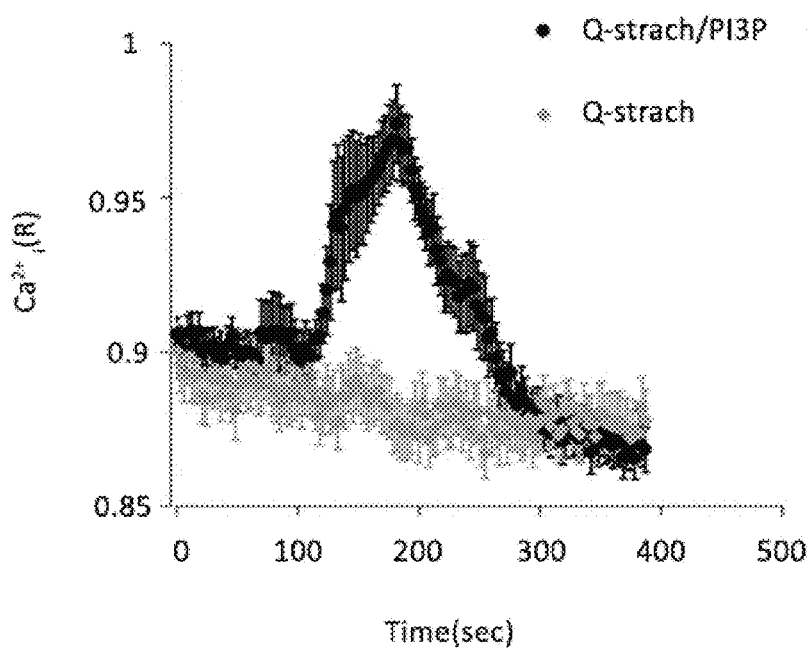
FIG. 9 shows a representative experiment showing the averaged Ca$^{2+}$ release over time in HEK 293 cells loaded with Fura-2 after application of Q-starch/PI3P complexes at N/P=2 ratio (black) and non-complexed Q-starch (gray), (0.9 mg/L, corresponding concentration for N/P=2). Results are presented as mean±SEM, (n>30).

Intracellular Ca$^{2+}$ release following exogenous PI3P delivery mediated by Q-starch was assessed using live cell imaging. HEK 293 cells were loaded with an intracellular Ca$^{2+}$-sensitive fluorescent dye Fura-2, and intracellular Ca$^{2+}$ levels were monitored following treatment with Q-starch/PI3P complexes. FIG. 8 shows that complexes at N/P=2 ratio succeeded in triggering Ca$^{2+}$ mobilization better then complexes at N/P=1 ratio, and the mobilization rate was comparable to that achieved by the Carrier 3/PI3P complexes. Selected plots for the difference in $Ca^{2+}$ mobilization rate between cells treated with N/P=2 complexes and non-complexed Q-starch are presented in FIG. 9.

Example 6: Intracellular Localization of $PIP_3$ in Fixed HaCat Cells 0.5 µL (0.6 µg/µL) of $PIP_3$, (Phosphatidylinositol 3,4,5-trisphosphate) MW-1204.84 g/mol was diluted with 98 µL of treated water and sonicated for 60 sec. Then incubated with 1.8 µL (0.4 µg/µL) Q-Starch DTAF (N/P-1-3) for 60 min to create a complex. The resulting solution was applied to HaCat cells grown on glass coverslips in 12-well plates.

Cells were also incubated with complexes of 0.5 µL (0.6 µg/µL) of fluorophore conjugated-$PIP_3$, (BODIPY-FL D-myo-Phosphatidylinositol 3,4,5-trisphosphate (PtdIns(3,4,5)$P_3$)) (Ex/Em-505/513) MW-1795.91 g/mol and neomycin as commercial control carrier at 1:1 molar ratio, $PIP_3$ (0.004 µg/µL), or Q-Starch DTAF (0.0075 µg/µL) alone. Cells were incubated with the treatments for 60 min. Following incubation cells were washed three times with ice-cold PBS and fixed for 15 min at 37° C. with 250 µL of 4% paraformaldehyde (PFA). Cells were washed three times in ice cold-PBS. Cell membranes were labeled by WGA, Alexa flour 555 conjugate (5 µg/µL) incubated for 10 minutes at room temperature. Excess fixative was quenched with 1 mL of 100 mM glycin. Coverslips were mounted on glass slides. Cellular imaging was performed using Zeiss LSM510 laser confocal microscope.

Figure 10:
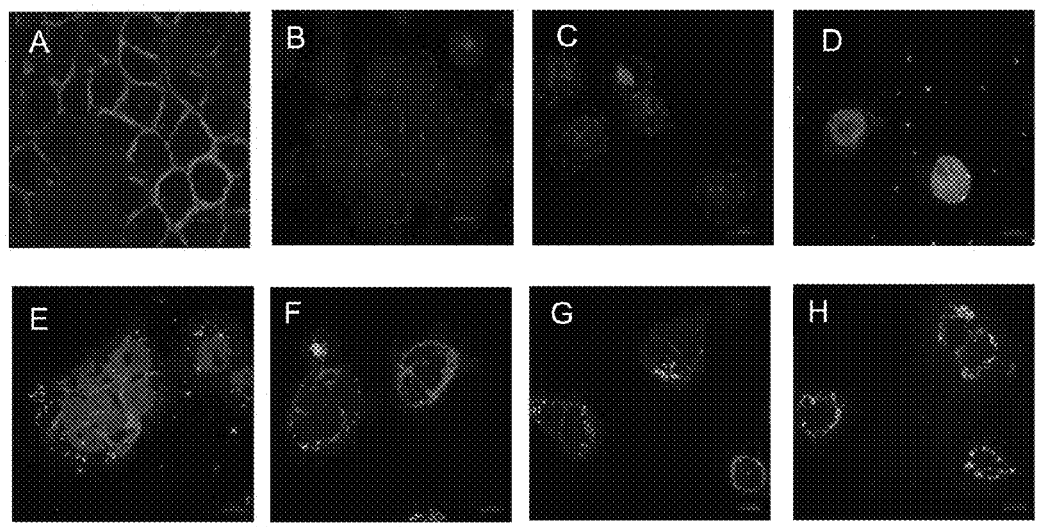
FIG. 10 shows confocal microscopic images of HaCat cellular uptake of complexes. A. Untreated cells; B. 60 min post incubation with Q-Starch$^{5\text{-}DTAF}$ C. 60 min post incubation with Neomycin/PIP$_3$. BODIPY-FL at 1:1 molar ratio; D-H. 60 min post incubation with Q-Starch$^{5\text{-}DTAF}$/PIP$_3$ complexes at D. N/P=1; E. N/P=1.5, F. N/P=2, G. N/P=2.5 and H. N/P=3. Membrane is labeled in red, nucleus labeled in blue and, Q-Starch$^{5\text{-}DTAF}$ or BODIPY-FL labeled in green.

The results are shown in FIG. 10. As can be seen from FIGS. 10D-10H, the higher the N/P ratio, the more complexes enter the cells. It can also be seen that the complexes at N/P ratios of 2 or above localize to the cell membranes, which corresponds to the location of the biological activity of PIP3. N/P=2 was therefore selected for additional experiments. It is further noted that complexes with the known carrier neomycin at a similar concentration (0.5 µm) did not enter the cells (as can be seen from FIG. 10C).

Example 7: Localization of Q-Starch/$PIP_3$ Complexes in HaCat Cells Over Time

HaCat cells seeded on glass cover-slip were washed three times with PBS. After that cells were exposed to $PIP_3$-Q-Starch DTAF at N/P=2 at distinct time periods (0, 3, 9, 15, 30, 45, 51, and 60) and were analyzed by live cells fluorescent microscopy.

Figure 11:
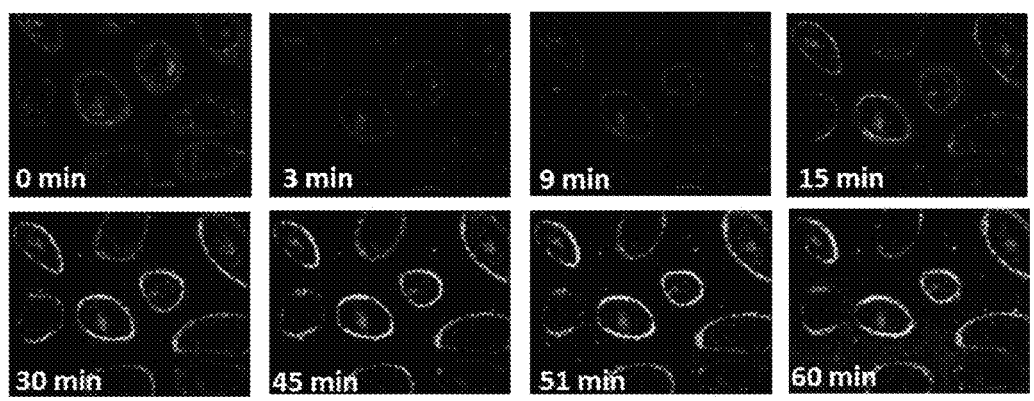
FIG. 11 shows localization of Q-starch/PIP$_3$ complexes overtime. HaCat cells grown on glass coverslips were imaged using confocal microscope over time after incubation with Q-Starch$^{5\text{-}DTAF}$ complexed with PIP$_3$ at N/P=2, 0.5 μM. Numbers are time lapsed, in minutes, from the beginning of incubation. Membrane is labeled in red, Q-Starch$^{5\text{-}DTAF}$ is labeled in green.

The results are shown in FIG. 11. Localization to membranes can be seen after 15 minutes of incubation, and already peaks at about 30 minutes.

REFERENCES

D. Fischer, T. Bieber, Y. Li, H. Elsasser, T. Kissel, A novel non-viral vector for DNA delivery based on low molecular weight, branched polyethylenimine: effect of molecular weight on transfection efficiency and cytotoxicity, Pharm. Res. 16 (1999) 1273-1279.

Geresh S., Dawadi, R. P., Arad S. M., Chemical modifications of biopolymers: quaternization of the extracellular polysaccharide of the red micralga Porphyridium sp. Carbohydrate polymers, 2000, 43: 75-80.

Godbey, W. T., Kenneth K. Wu, and Antonios G. Mikos. "Poly (ethylenimine)-mediated gene delivery affects endothelial cell function and viability." Biomaterials 22.5 (2001): 471-480.

Ishiki M., Randhawa V. K., Poon V., Jebailey L., Klip A., Insulin regulates the membrane arrival, fusion, and C-terminal unmasking of glucose transporter-4 via distinct phosphoinositides. J Biol Chem., 2005, 280(31):28792-802.

Jiang T., Sweeney G., Rudolf M. T., Klip A., Traynor-Kaplan A., Tsien R. Y. Membrane-permeant esters of phosphatidylinositol 3,4,5-trisphosphate. J Biol Chem., 1998, 273(18):11017-24.

Payrastre, Bernard, et al. "Phosphoinositides: key players in cell signalling, in time and space." *Cellular signalling* 13.6 (2001): 377-387.

Patel N., Rudich A., Khayat Z. A., Garg R., Klip A., Intracellular segregation of phosphatidylinositol-3,4,5-trisphosphate by insulin-dependent actin remodeling in L6 skeletal muscle cells. Mol Cell Biol., 2003, 23(13):4611-26.

Sieradzki R., Traitel T., Goldbart R., Geresh S., Kost J., Development and characterization of quaternized starch as a carrier for gene therapy applications, 2008, PhD thesis.

Stephen K. Dove, et al. Osmotic stress activates phosphatidylinositol-3, 5-bisphosphate synthesis. Nature, 1997, 390.6656: 187-192.

Strawbridge, Andrew B., and Jeffrey S. Elmendorf. "Phosphatidylinositol 4, 5-Bisphosphate Reverses Endothelin-1-Induced Insulin Resistance via an Actin-Dependent Mechanism." Diabetes 54.6 (2005): 1698-1705.

Sweeney G., Garg R. R., Ceddia R. B., Li D., Ishiki M., Somwar R., Foster L. J., Neilsen P. O., Prestwich G. D., Rudich A., Klip A., Intracellular delivery of phosphatidylinositol (3,4,5)-trisphosphate causes incorporation of glucose transporter 4 into the plasma membrane of muscle and fat cells without increasing glucose uptake. J Biol Chem., 2004, 279(31):32233-42.

Vicinanza M. et al. "PI (5) P regulates autophagosome biogenesis." Molecular cell 57.2 (2015): 219-234.

Yamashita, S. I., Oku, M., and Sakai, Y. (2007). Functions of PI4P and sterol glucoside are necessary for the synthesis of a nascent membrane structure during pexophagy. Autophagy 3, 35-37.

The invention claimed is:

1. A complex comprising at least one phosphoinositide and at least one positively charged modified polysaccharide, wherein said positively charged modified polysaccharide is quaternized starch, wherein the molar ratio of positively charged amine groups on said at least one positively charged modified polysaccharide to negatively charged phosphate groups in the at least one phosphoinositide is at least 2.

2. The complex according to claim 1, wherein the molecular weight of said quaternized starch is in a range selected from the group consisting of $10^3$ to $10^8$ daltons, $10^4$ to $10^5$ daltons, and $10^4$ to $5 \times 10^4$ daltons, or the molecular weight is about 26,500 daltons.

3. The complex according to claim 1, wherein said phosphoinositide is selected from the group consisting of phosphatidylinositol 3-phosphate (PI3P), phosphatidylinositol 4-phosphate (PI4P) phosphatidylinositol 5-phosphate (PI5P), phosphatidylinositol 3,4-bisphosphate (PI(3,4)$P_2$), phosphatidylinositol 3,5-bisphosphate (PI(3,5)$P_2$), phosphatidylinositol 4,5-bisphosphate (PI(4,5)$P_2$), and phosphatidylinositol 3,4,5-trisphosphate (PI(3,4,5)$P_3$ or $PIP_3$).

4. The complex according to claim 3, wherein said phosphoinositide is PI3P or $PIP_3$.

5. The complex according to claim 1, wherein the molar ratio of the positively charged amine groups on said at least one positively charged modified polysaccharide to the negatively charged phosphate groups in the at least one phosphoinositide is about 2.

6. The complex according to claim 1 in the form of a nanoparticle.

7. The complex according to claim 1, further comprising a targeting ligand.

8. A method for enhanced localization of a phosphoinositide to cell membranes, comprising contacting cells with a complex comprising at least one phosphoinositide and at least one positively charged modified polysaccharide, wherein said positively charged modified polysaccharide is quaternized starch, and wherein the molar ratio of positively charged amine groups on said at least one positively charged modified polysaccharide to negatively charged phosphate groups in the at least one phosphoinositide is at least 2; or a pharmaceutical composition comprising the complex.

9. The method of claim 8, wherein said cells are mammalian cells, including muscle cells, liver cells, fat cells, macrophages, keratinocytes, or stem cells.

* * * * *